United States Patent [19]
Sprecker et al.
[11] Patent Number: 4,756,840
[45] Date of Patent: Jul. 12, 1988

[54] BETA-ALKYLIDENE PHENETHYL ALCOHOLS, ORGANOLEPTIC USES THEREOF AND PROCESSES FOR PREPARING SAME

[75] Inventors: Mark A. Sprecker, Sea Bright; Robert P. Belko, Woodbridge, both of N.J.

[73] Assignee: International Flavors & Fragrances Inc., New York, N.Y.

[21] Appl. No.: 92,756

[22] Filed: Sep. 3, 1987

[51] Int. Cl.[4] .......................... C11B 9/00; A61K 7/46

[52] U.S. Cl. ...................................... 252/8.6; 512/20; 252/174.11; 523/102; 568/813; 568/862; 568/880; 568/881

[58] Field of Search ................. 252/8.6; 568/813, 862; 512/20; 523/102

*Primary Examiner*—Paul Lieberman
*Assistant Examiner*—Isabelle Rodriguez
*Attorney, Agent, or Firm*—Arthur L. Liberman

[57] ABSTRACT

Described is the novel compound genus, the beta-alkylidene phenethyl alcohols of our invention, defined according to the generic structure:

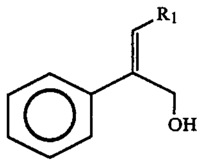

(wherein $R_1$ represents hydrogen or methyl, useful in augmenting or enhancing the aroma of consumable materials including perfumes, colognes and perfumed articles including solid or liquid anionic, cationic, nonionic or zwitterionic detergents, fabric softener articles, fabric softener compositions, cosmetic powders and hair preparations).

9 Claims, 9 Drawing Sheets

GLC PROFILE FOR EXAMPLE I(A).

GLC PROFILE FOR EXAMPLE I(A).

NMR SPECTRUM FOR EXAMPLE I(A).

GLC PROFILE FOR EXAMPLE I(A).

NMR SPECTRUM
FOR EXAMPLE I(A).

GLC PROFILE FOR EXAMPLE I(B).

NMR SPECTRUM FOR EXAMPLE I(B).

GLC PROFILE FOR EXAMPLE II.

NMR SPECTRUM FOR EXAMPLE I.

BETA-ALKYLIDENE PHENETHYL ALCOHOLS, ORGANOLEPTIC USES THEREOF AND PROCESSES FOR PREPARING SAME

BACKGROUND OF THE INVENTION

This invention relates to beta-alkylidene phenethyl alcohols defined according to the generic structure:

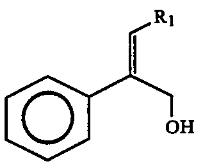

wherein $R_1$ represents hydrogen or methyl and uses thereof in augmenting or enhancing the aroma of perfume compositions or perfumed articles including perfumed polymers.

Materials which can provide lilac, rose, hyacinth, peony, green, cinnamon, honey and floral aromas with intense green, lilac, rose and hyacinth undertones particularly those materials which are relatively inexpensive are highly sought after in the art of perfumery. Many of the natural materials which provide such fragrance profiles and contribute desired nuances to perfumery compositions and perfumed articles are high in cost, vary in quality from one batch to another and/or are generally subject to the usual variations of natural products.

There is accordingly, a continuing effect to find synthetic materials which will replace the essential fragrance notes produced by natural essential oils or compositions thereof. Unfortunately, many of these synthetic materials either have the desired nuances only to a relatively small degree or else contribute undesirable or unwanted odor to the composition. The search for more materials which can provide a more refined lilac, rose, hyacinth, peony, green, cinnamon, honey and floral aroma with intense green, lilac, rose and hyacinth undertones has been difficult and relatively costly in the areas of both natural products and synthetic products.

Aryl alkanols are known to perfumery materials particularly the well known phenylethyl alcohol which provides rose, cinnamon and honey aromas to floral fragrance formalations and perfumed articles.

Beta-methylene phenethyl acetate having the structure:

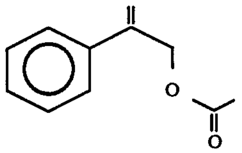

is disclosed to provide sweet, lilac, hyacinth and ripe grain aromas to perfumed articles and perfumed formulations in Canadian Letters Pat. No. 1,157,036 issued on Nov. 15, 1983 as well as European Pat. No. 035,183 published on Feb. 20, 1981. The said European and Canadian Patents also disclose other esters of methylene phenethyl alcohol useful in perfumery but do not disclose that the alcohol itself is so useful.

Indeed, the alkylidene phenethyl alcohols of our invention have unexpected, unobvious and advantageous intense aromas and give rise to unexpected, unobvious and advantageous properties with respect to perfume compositions, perfumed articles and perfumed polymers.

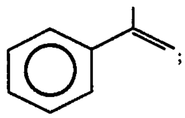;

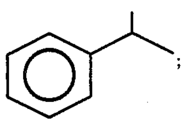;

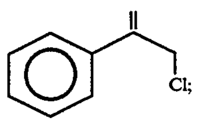;

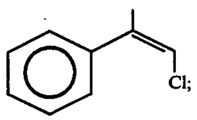;

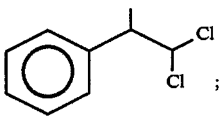;

and $CHCl_3$.

Figure 2:
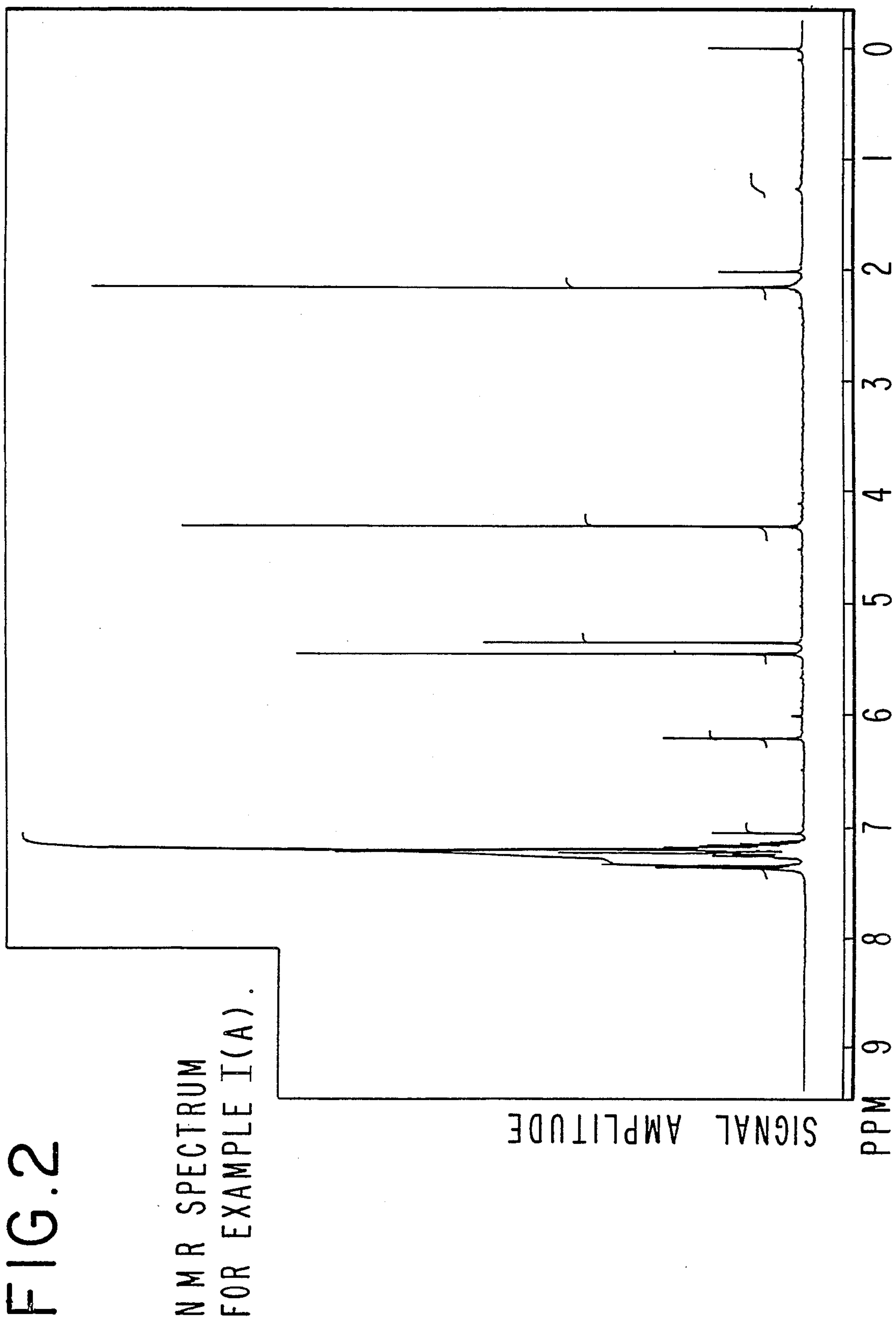

FIG. 2 is the NMR spectrum for the distillation product of the reaction product of Example I(A) containing the compounds having the structures:

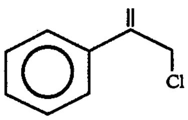 and 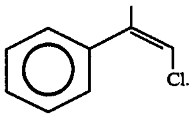.

Figure 3:
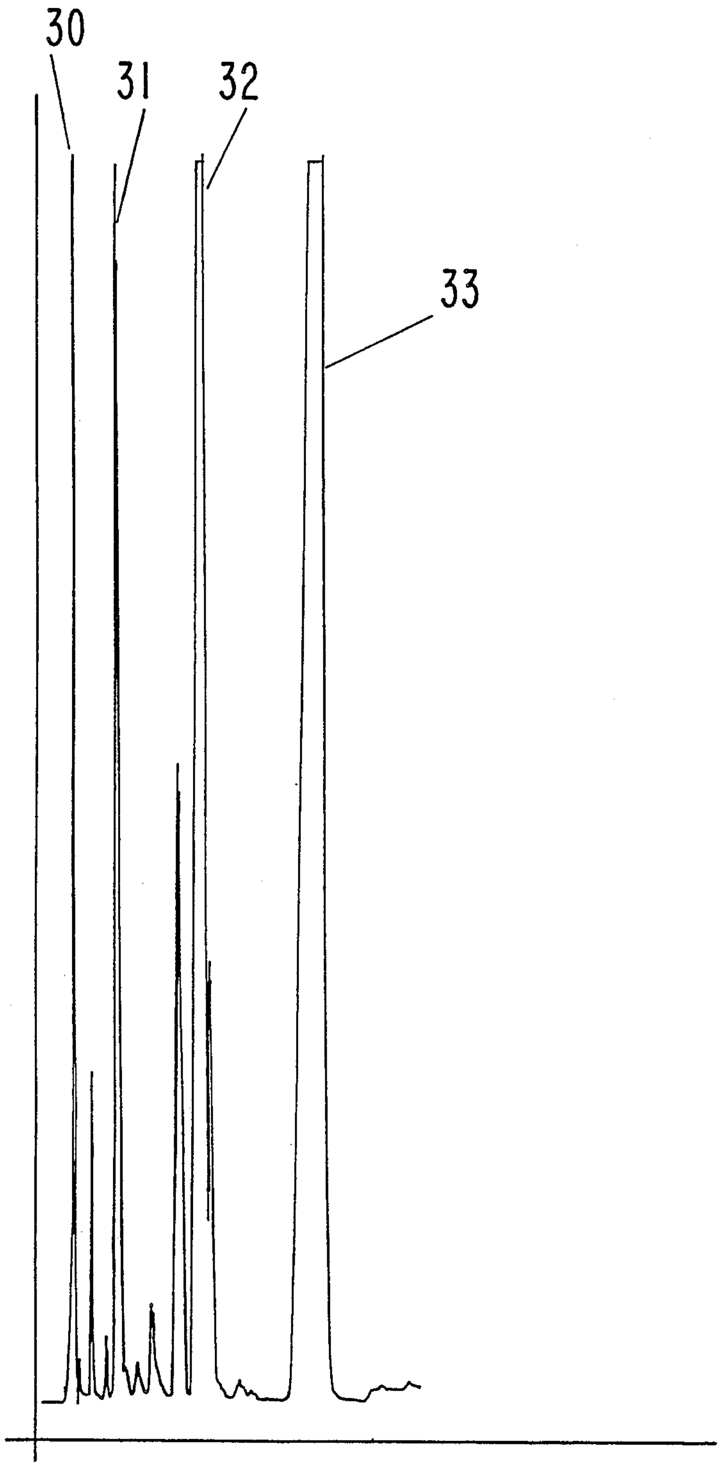

FIG. 3 is the GLC profile for the second step (second reaction) of Example I containing the compounds having the structures:

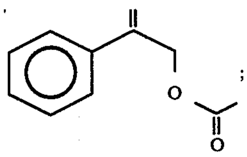;

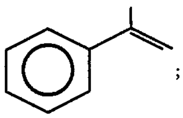;

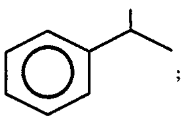;

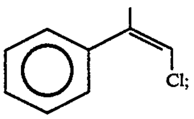;

and $CHCl_3$.

Figure 4:
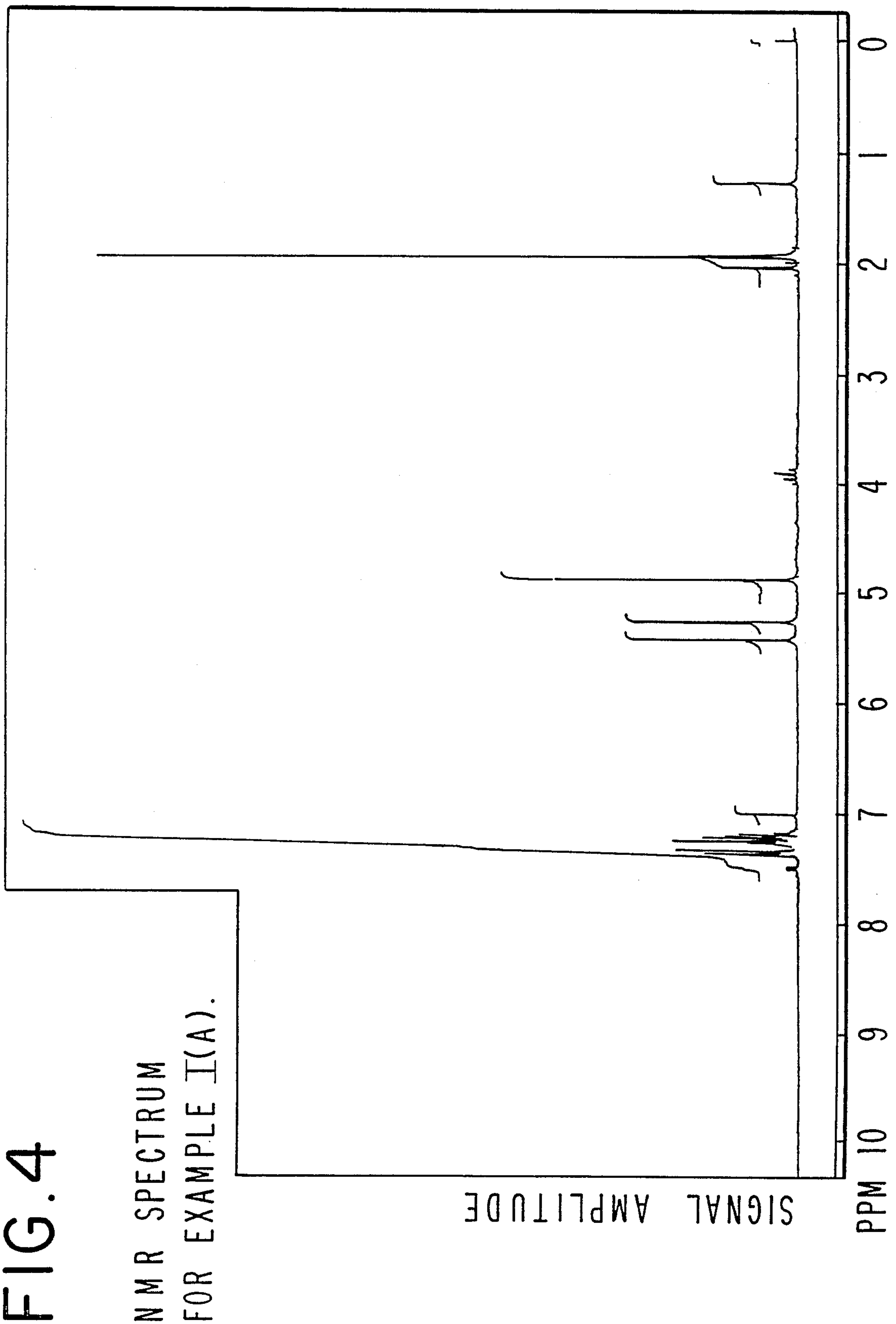

FIG. 4 is the NMR spectrum for the compound having the structure:

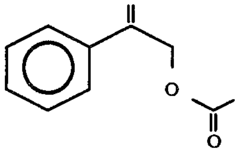

produced according to the second step of Example I(A).

Figure 5:
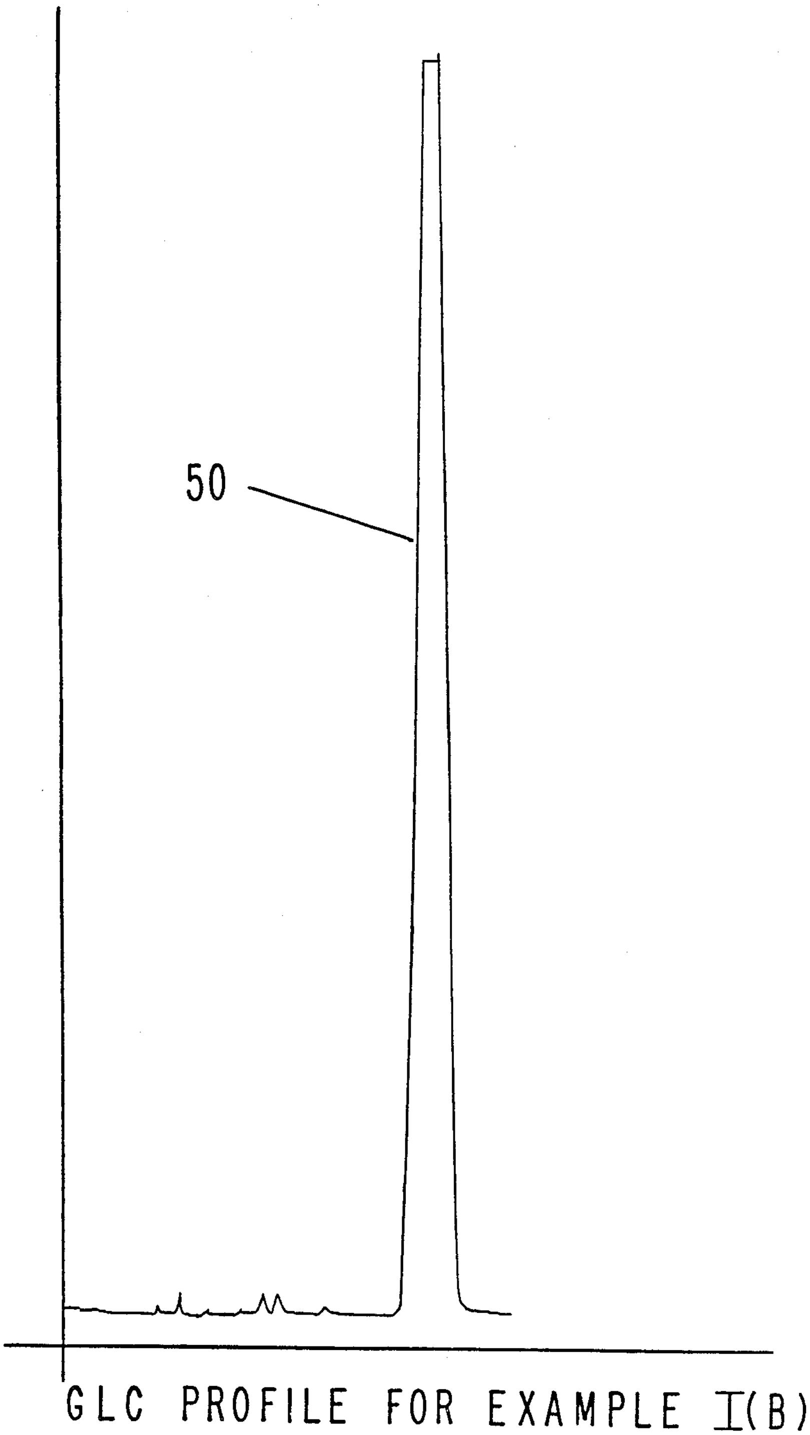

FIG. 5 is the GLC profile for the reaction product of Example I(B) containing the compound having the structure:

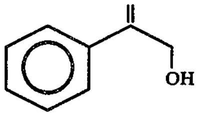

(Conditions: SE-30 column programmed at 180° C. isothermol).

Figure 6:
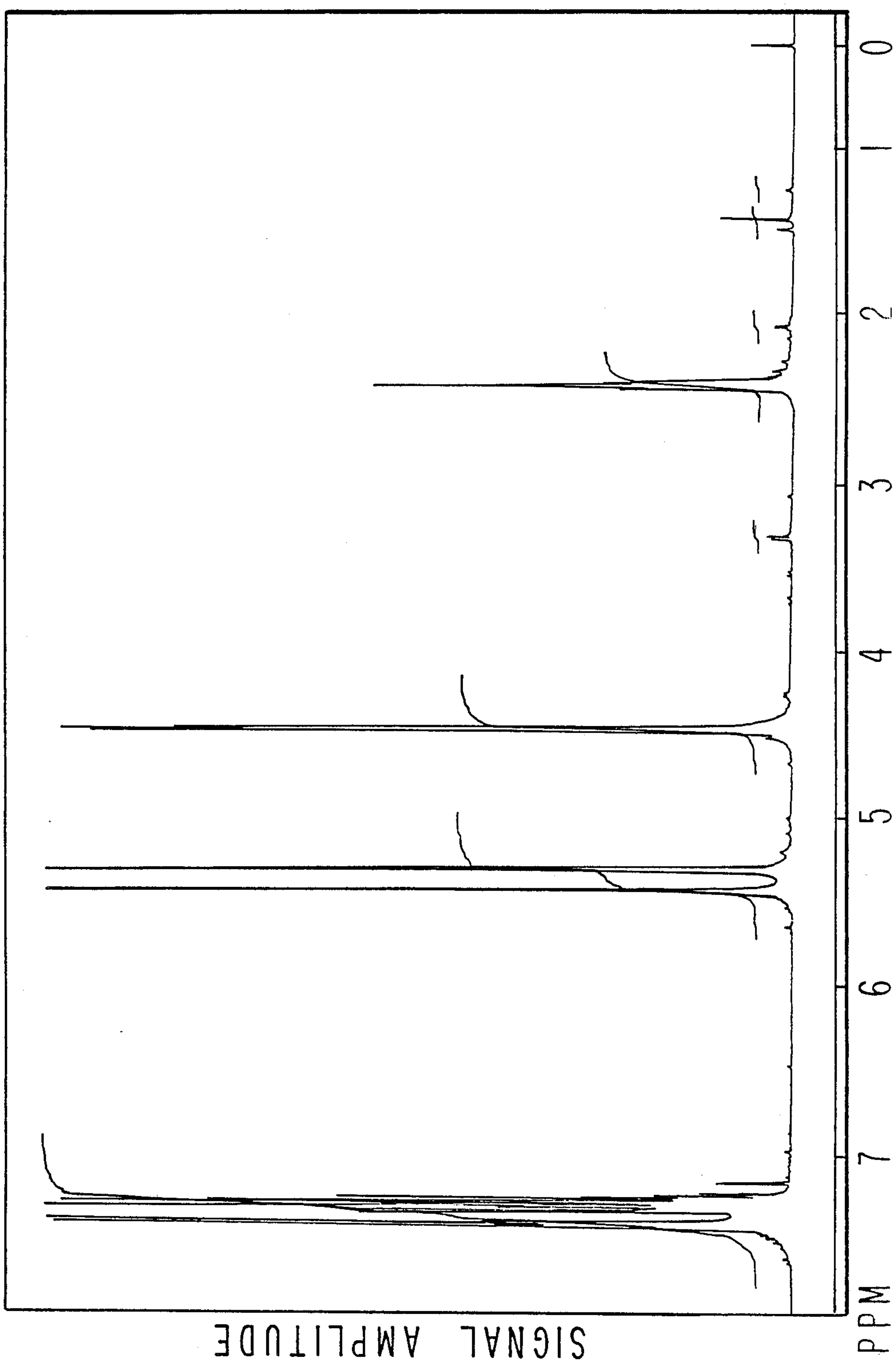

FIG. 6 is the NMR spectrum for the compound having the structure:

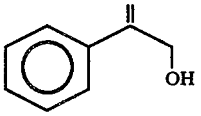

produced according to Example I(B).

Figure 7:
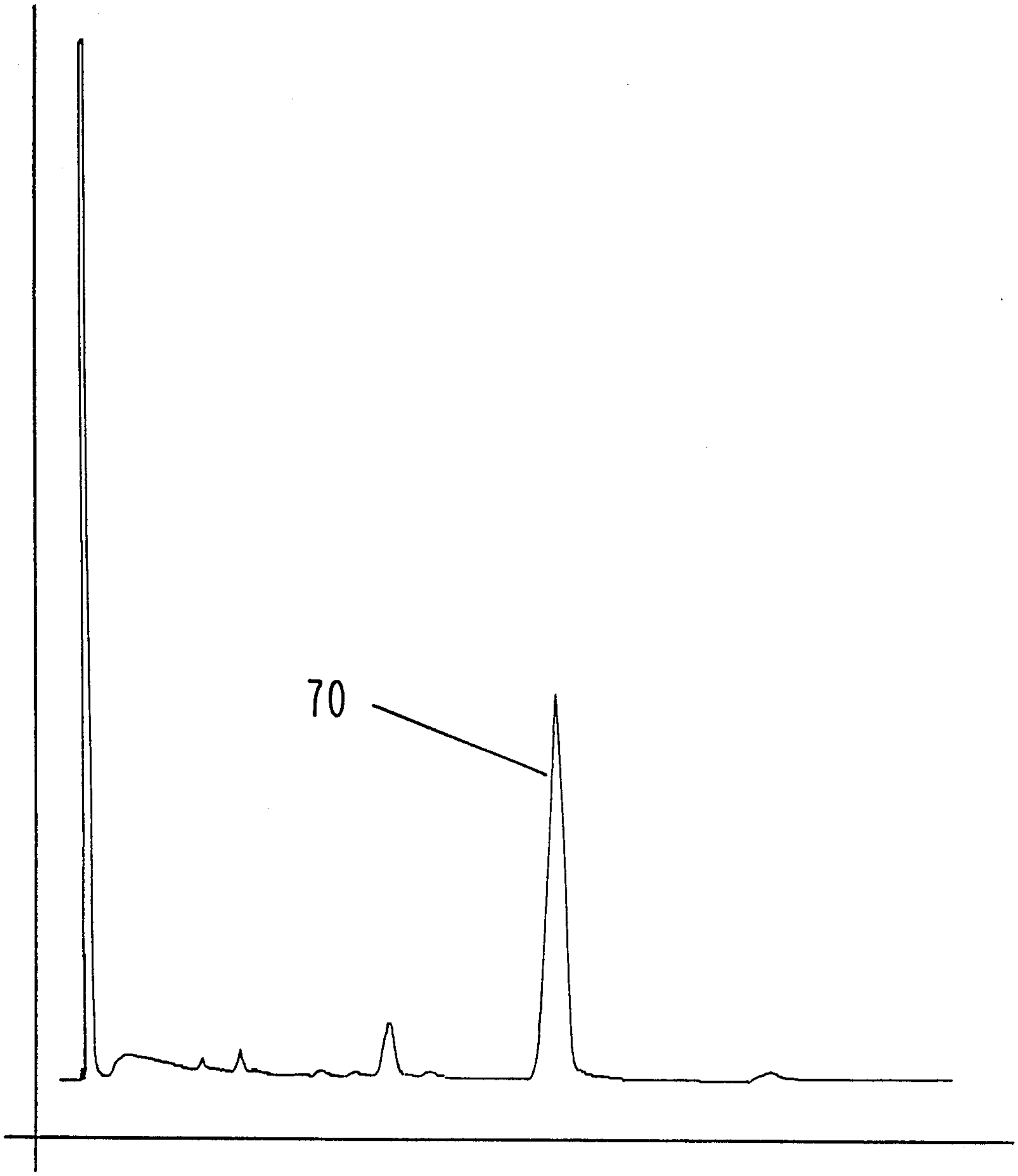

FIG. 7 is the GLC profile for the reaction product of Example II containing the compound having the structure:

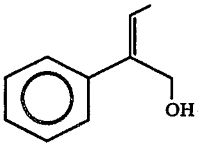

(Conditions: Carbowax column programmed at 180° C. isothermol).

Figure 8:
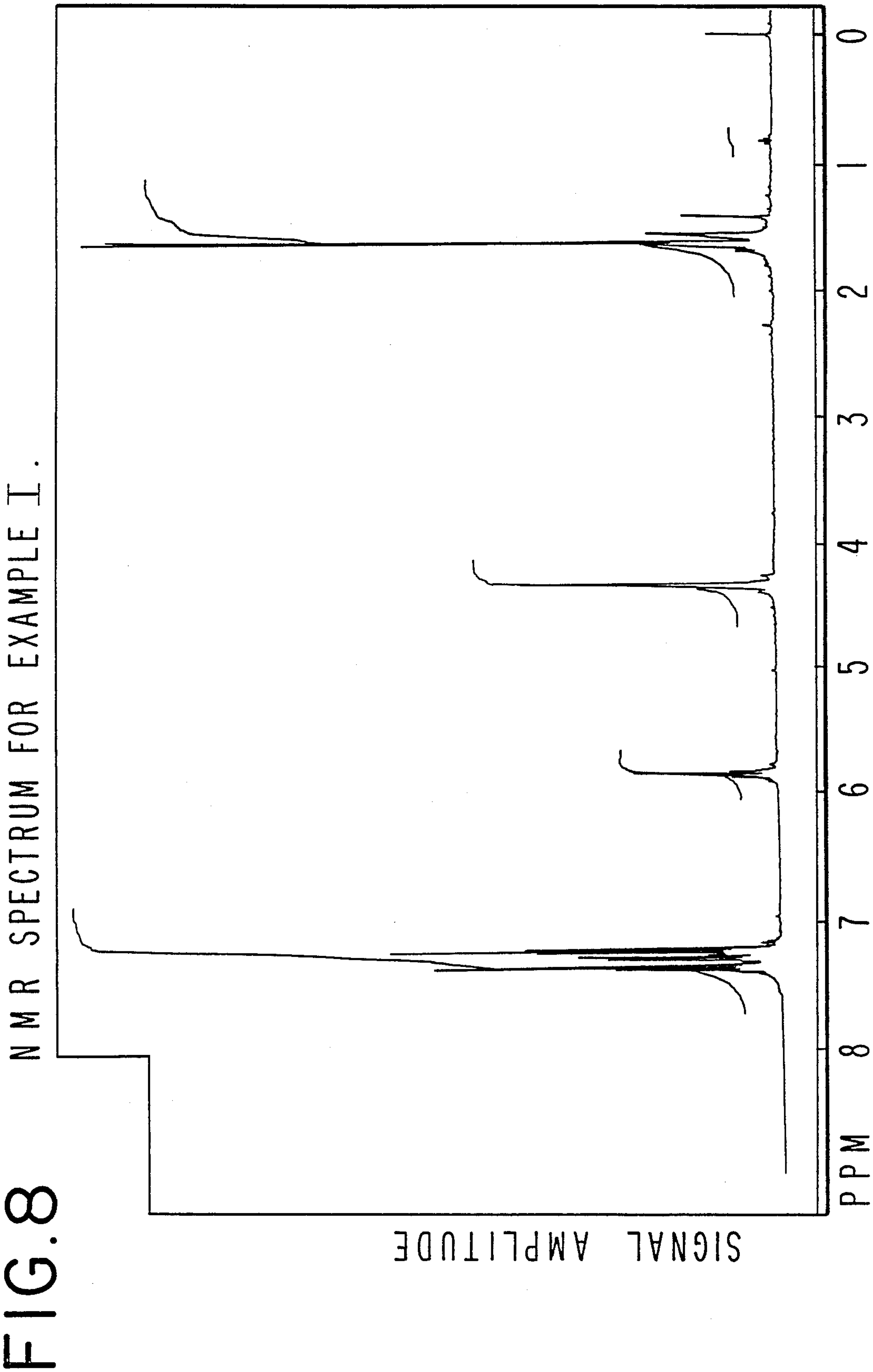

FIG. 8 is the NMR spectrum for the compound having the structure:

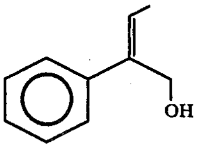

produced according to Example II.

Figure 9:
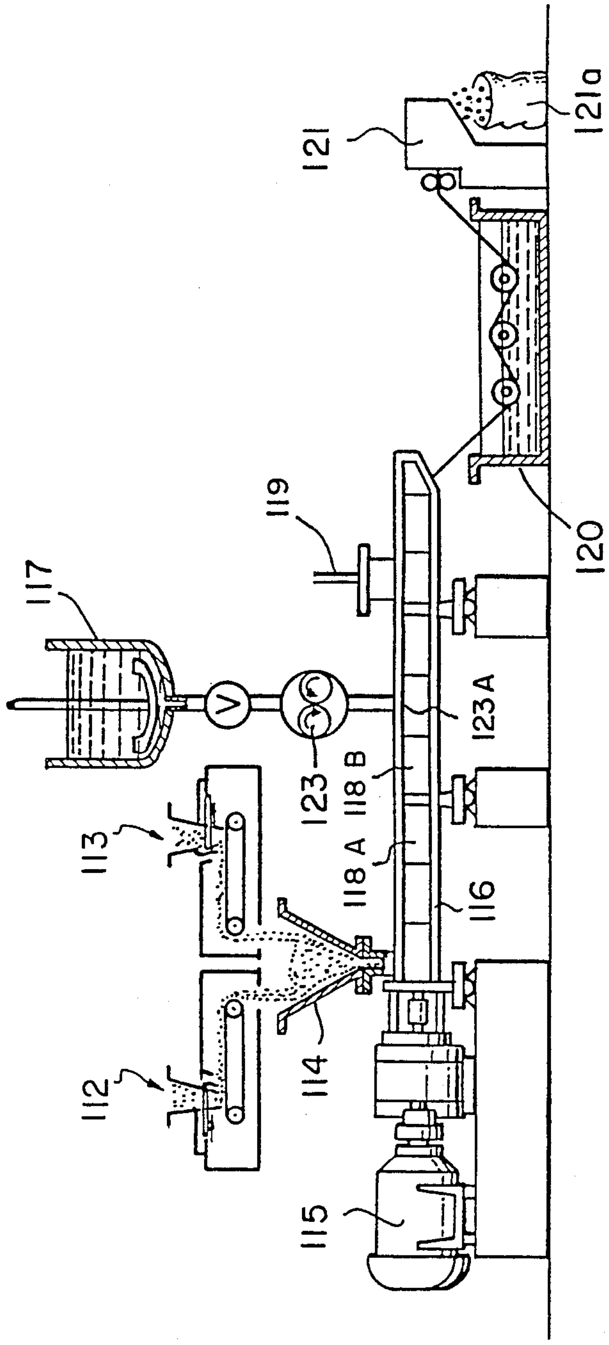

FIG. 9 is a cut-away side elevation schematic diagram of a screw extruder during the compounding of resin with one or more of the beta-alkylidene phenethyl alcohols of our invention while simultaneously adding foaming agent into a hollow portion of the barrel of the extruder and incorporates pelletizing apparatus used in pelletizing the extruded foamed tow produced as a result of the extrusion operation.

DETAILED DESCRIPTION OF THE DRAWINGS

Figure 1:
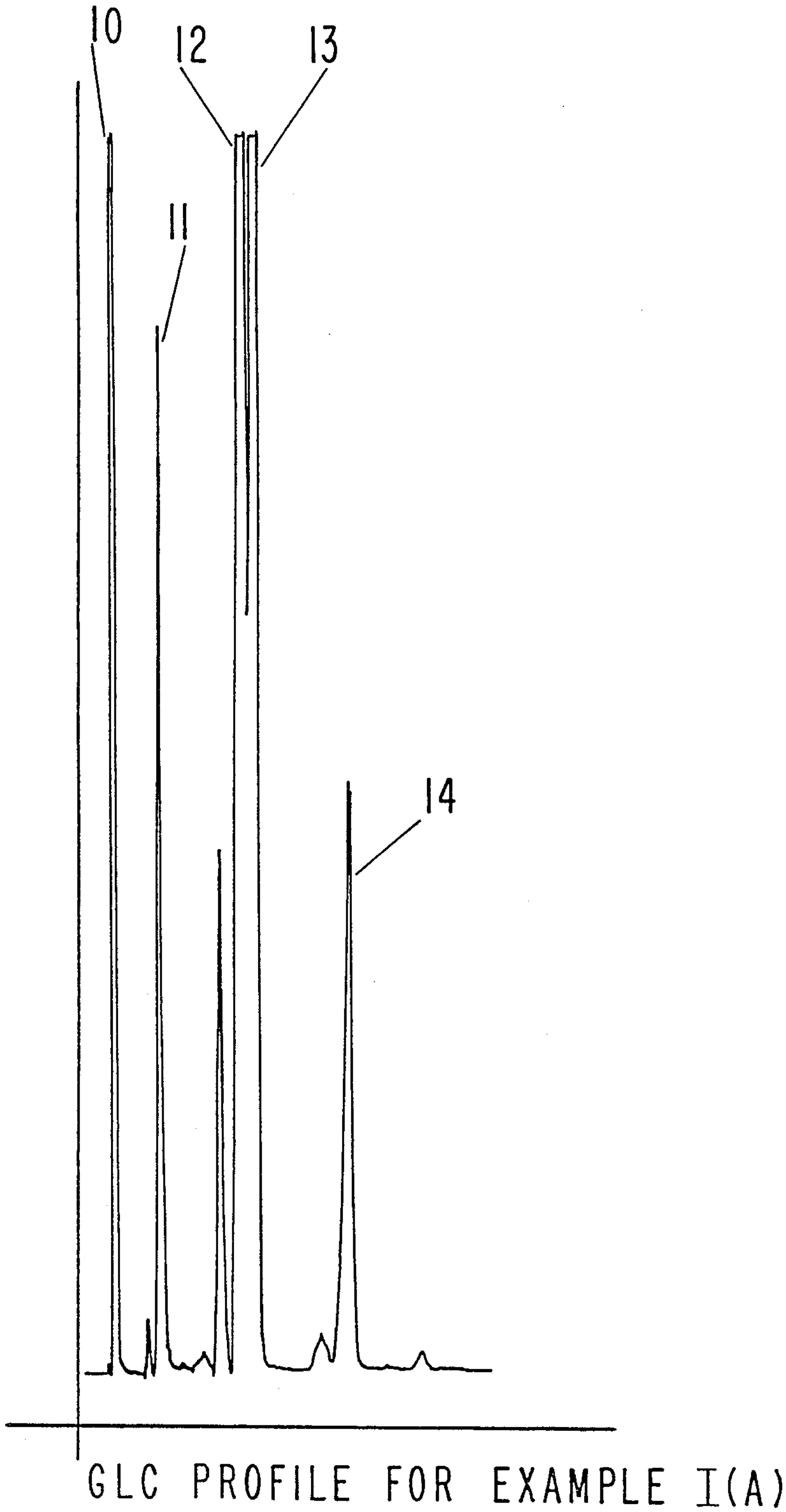
FIG. 1 is the GLC profile for the reaction product of Example I(A) containing the compounds having the structures.

FIG. 1 is the GLC profile for the reaction product of the first step of Example I(A) employing the reaction:

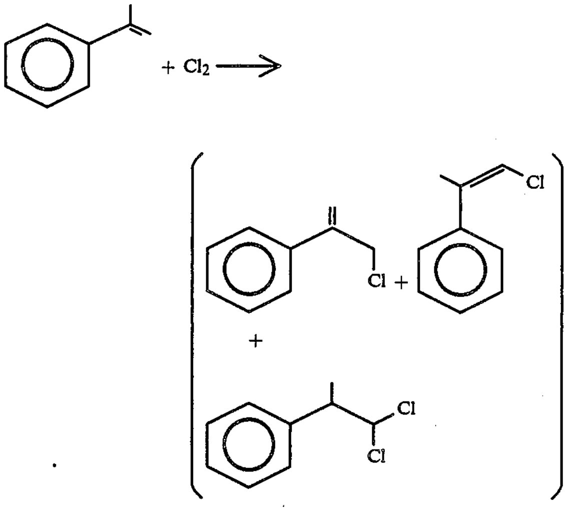

.

(Conditions: SE-30 column programmed at 180° C. isothermol). The peak indicated by reference numeral 10 is the peak for $CHCl_3$. The peak indicated by reference numeral 11 is the peak for the compounds having the structures:

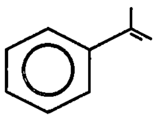

and

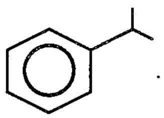

.

The peak indicated by reference numeral 12 is the peak for the compound having the structure:

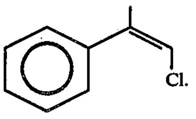

The peak indicated by reference numeral 13 is the peak for the compound having the structure:

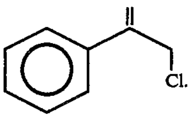

The peak indicated by reference numeral 14 is the peak for the compound having the structure:

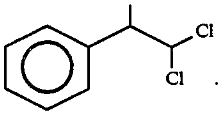

FIG. 3 is the GLC profile for the reaction product (second step) of Example I(A) resulting from the reaction:

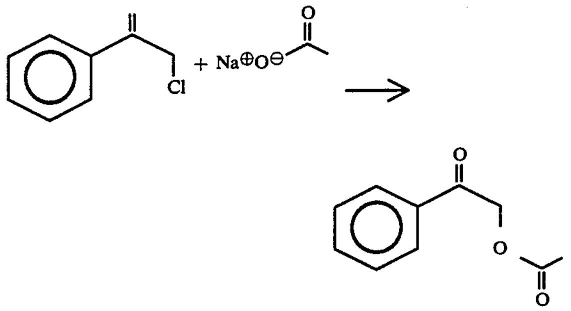

(Conditions: SE-30 column programmed at 180° C. isothermol). The peak indicated by reference numeral 30 is the peak for $CHCl_3$. The peak indicated by reference numeral 31 is the peak for the compounds having the structures:

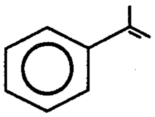
and
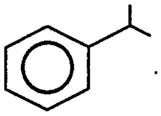
.

The peak indicated by reference numeral 32 is the peak for the compound having the structure:

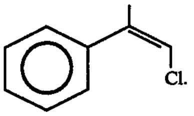

The peak indicated by reference numeral 33 is the peak for the compound having the structure:

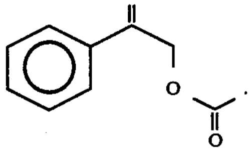

FIG. 5 is the GLC profile for the reaction product of Example I(B) the reaction being:

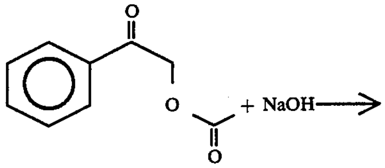

The peak indicated by reference numeral 50 is the peak for the compound having the structure:

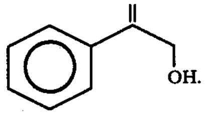

(Conditions: SE-30 column programmed at 180° C. isothermol).

FIG. 7 is the GLC profile for the reaction product (crude) of Example II, the reaction product resulting from the reaction:

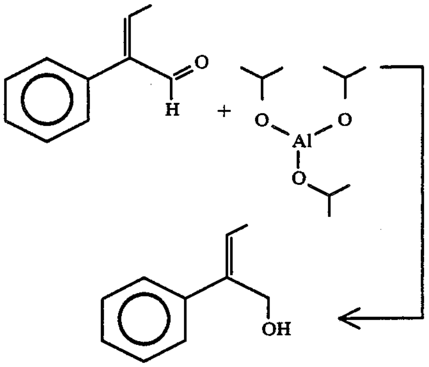

(Conditions: Carbowax column programmed at 180° C. isothermol). The peak indicated by reference numeral 70 is the peak for the compound having the structure:

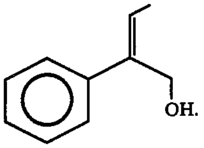

FIG. 9 is a schematic cut-away elevation diagram of extrusion and pelletizing apparatus useful in carrying out a process of our invention during the operation of said apparatus whereby perfuming material containing one of the beta-alkylidene phenethyl alcohols of our inventon (and, optionally, at least one other perfumery ingredient) is incorporated into a resin such as polyethylene. Motor 115 drives the extruder screws located at 123A in barrel 116, the extruder being operated at temperatures in the range of from about 150 up to about 250° C. At the beginning of the barrel, resin at source 112 together with additives, e.g., opacifiers, processing aids, colors, pearlescent agents and densifiers at location 113 is added via addition funnel 114 into the extruder. Simultaneously (when the operation reaches "steady state"), a perfumant containing one of the beta-alkylidene phenethyl alcohols of our invention together with, optionally, at least one other perfumery ingredient, is added to the extruder at one, two or more of barrel segments 3-8 of the extruder (which may be a twin screw or single screw extruder) at locations 118*a*, 118*b*, 118*c* and 118*d* by means of gear pump 123 from source 117. From source 119 into barrel segments 5-10, gaseous or liquid blowing agents, e.g., nitrogen, carbon dioxide and the like are added simultaneously with the addition of the perfumant containing one or more of the beta-alkylidene phenethyl alcohols of our invention.

The feed rate range of resin is about 80-300 pounds per hour. The feed rate range of the perfumant containing one or more of the beta-alkylidene phenethyl alcohols of our invention is between 1 and 35% of the feed rate range of the resin. The blowing agent rate range is such that the pressure of the gas or the pressure over the perfumant containing one or more of the beta-alkylidene phenethyl alcohols of our invention being fed into the extruder is between about 50 and 200 psig. If desired, the extruded ribbon (122) or cylinder may be passed through a water bath 120 and pelletizer 121 into collection apparatus 121A.

THE INVENTION

It has now been determined that the beta-alkylidene phenethyl alcohols defined according to the structure:

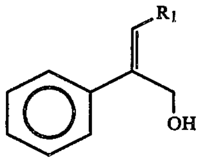

wherein $R_1$ is hydrogen or methyl are capable of imparting or augmenting a variety of fragrances to various consumable materials including fragrance compositions, colognes, perfumed polymers and perfumed articles.

The beta-alkylidene phenethyl alcohols of our invention include the compounds having the structures:

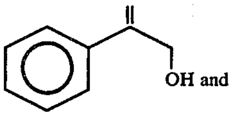
and
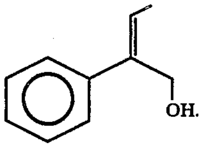
.

The compound having the structure:

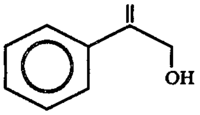

has a lilac, rose, hyacinth, peony, green, cinnamon and honey aroma profile with intense green, lilac, rose and hyacinth undertones. The compound having the structure:

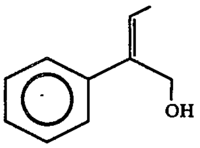

has an intense green and floral aroma with green, rose undertones.

The compound having the structure:

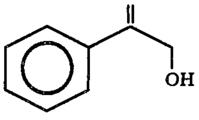

may be prepred by first reacting alpha-methyl styrene having the structure:

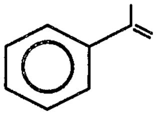

with a halogen such as chlorine according to the generic reaction:

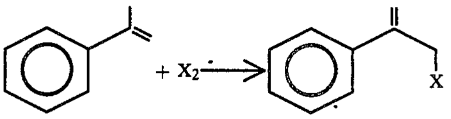

wherein X represents chloro or bromo (which includes the specific reaction and the preferred reaction:

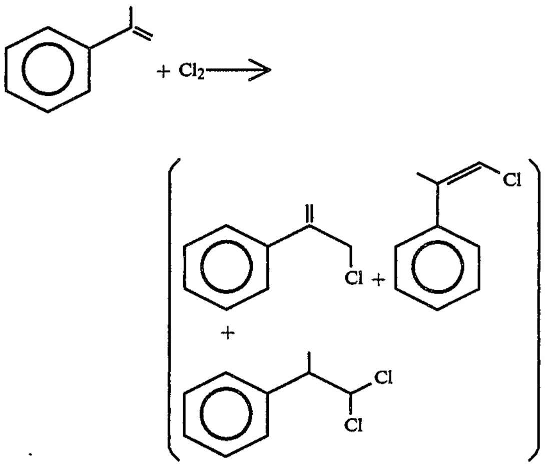

The resulting alpha-methylene phenethyl halide is then reacted with an alkali metal salt of an alkanoic acid according to the reaction:

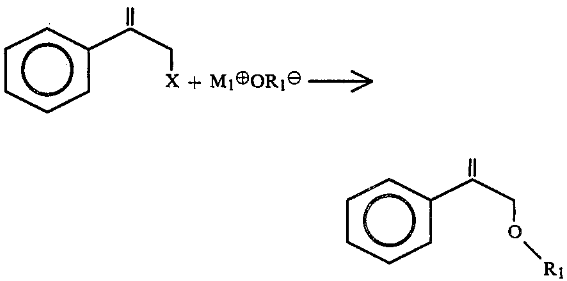

wherein X is chloro or bromo; $R_1$ represents $C_2$-$C_5$ acyl and $M_1$ represents alkali metal including sodium, potassium and lithium. The foregoing reaction includes the more specific reactions, to wit:

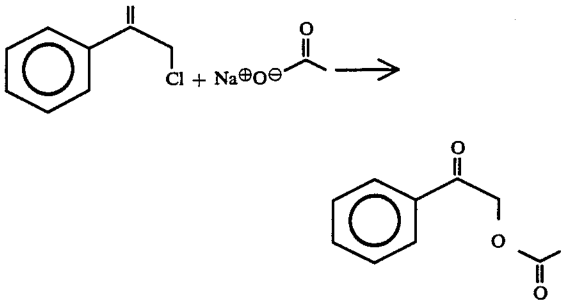

and

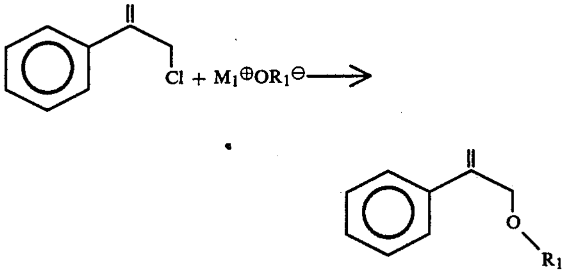

using the preferred chloro derivatives and using the preferred sodium acetate reactant.

The resulting ester having the structure:

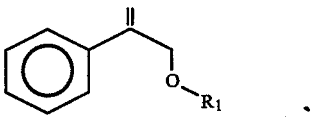

is then saponified with an alkali metal hydroxide according to the generic reaction:

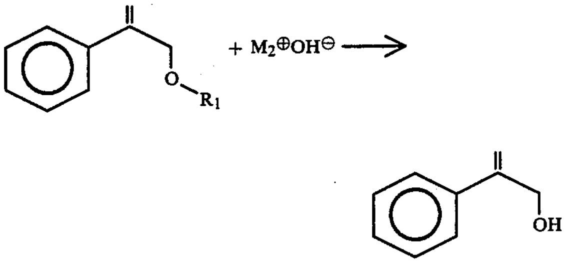

wherein $M_2$ is the same or different from $M_1$ and represents alkali metal including lithium, potassium or sodium. This generic reaction includes the specific reaction and the preferred reaction:

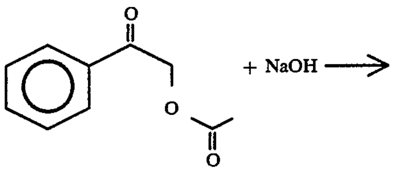

-continued

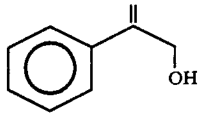

The compound having the structure:

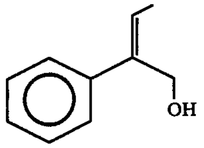

may be prepared by first reacting the aldehyde having the structure:

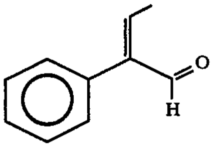

with an appropriate reducing agent, in this case aluminum triisopropylate according to the reaction:

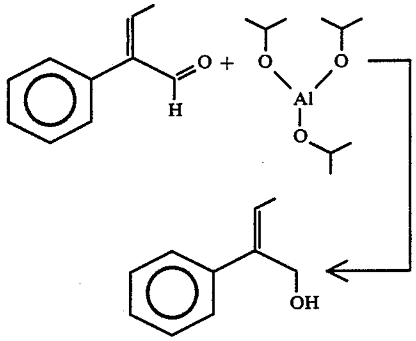

In carrying out the first part of the reaction leading towards the preparation of the compound having the structure:

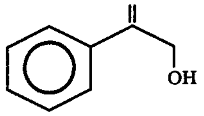

that is, the reaction, to wit:

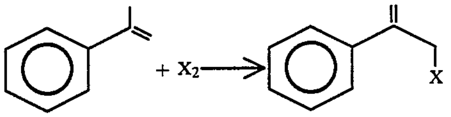

wherein X represents chloro or bromo, the reaction is carried out in the presence of an alkali metal carbonate such as and preferably sodium carbonate and in the presence of an inert solvent, preferably methylene dichloride. The reaction is carried out at a temperature in the range of from about 20° C. up to about 40° C. The halogen, e.g., the chlorine or the bromine is either fed (in the case of chlorine gas) or admixed (in the case of bromine liquid) into the mixture of the alkali metal carbonate, the alpha-methyl styrene and the methylene dichloride while maintaining the temperature in the range of 20°-40° C.

The second step of the reaction, to wit, the reaction:

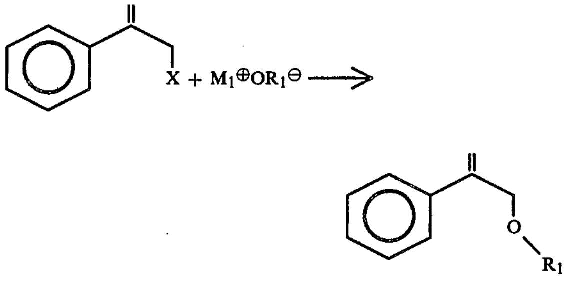

is carried out using an alkali metal acylate, preferably sodium acetate in the presence of a phase transfer agent such as an ALIQUAT phase transfer agent defined in U.S. Pat. No. 4,010,207 which ALIQUATE phase transfer agents are quaterny ammonium salts. This reaction takes place at a temperature in the range of from about 70° C. up to about 100° C.

The resulting ester product is defined according to the structure:

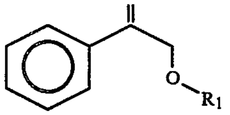

wherein $R_1$ represents $C_2$-$C_5$ acyl is then fractionally distilled and saponified using an alkali metal hydroxide such as sodium hydroxide preferably in the presence of a lower alkanol such as methyl alcohol. The reaction is carried out preferably at atmospheric pressure to reflux conditions, e.g., 90° C.-100° C. for a period of between about 2 and 6 hours. At the end of the reaction, the reaction product is washed with water and fractionally distilled yielding the product having the structure:

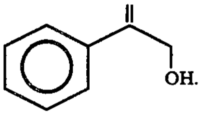

The compound having the structure:

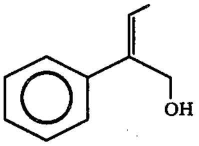

on the other hand is prepared according to the reaction:

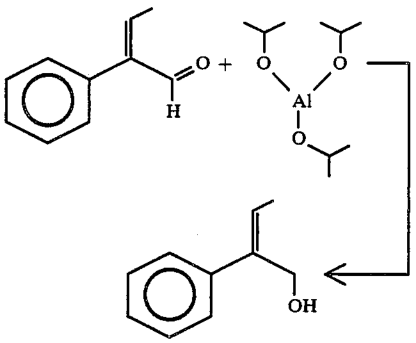

The aldehyde having the structure:

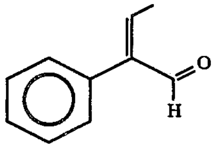

is reacted with aluminum triisopropylate at reflux conditions (e.g., about 110°-140° C.). Initially, the aluminum triisopropylate is admixed with isopropyl alcohol. The aldehyde having the structure:

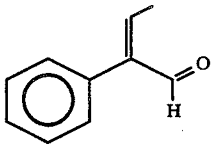

is then added to the aluminum triisopropylate mixture while the aluminum triisopropylate/isopropanol mixture is being refluxed. The reaction time varies from about 5 hours up to about 10 hours and the reaction temperature varies from about 110° C. up to about 140° C. At the end of the initial reaction, the reaction product is admixed with toluene and an aqueous alkali metal hydroxide such as 50% aqueous sodium hydroxide and the reaction mass is refluxed for a period of between about 0.5 hours up to about 2 hours. The reaction mass is then cooled to room temperature and washed with dilute base, e.g., 5% sodium hydroxide. The reaction mass is then distilled using a fractionation column at a vapor temperature in the range of 80°-90° C. and a pressure in the range of from about 2.1 up to about 2.5 mm/Hg.

With reference to the reaction, to wit:

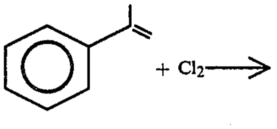

-continued

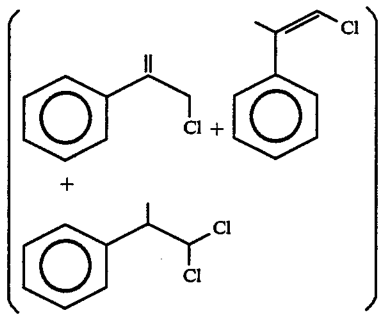

the mole ratio of chlorine to alpha-methyl styrene may vary from about 1:1 down to about 0.5:1 and the temperature of this specific reaction may vary from about 0° C. up to about 50° C. The reaction may be carried out in a solvent or in the absence of a solvent. When a solvent is used a hydrocarbon or chlorocarbon solvent is useful. The reaction may be carried out in the presence of an alkali metal carbonate or bicarbonate, e.g., potassium carbonate, sodium carbonate, lithium carbonate, potassium bicarbonate, sodium bicarbonate or lithium bicarbonate.

With reference to the reaction, to wit:

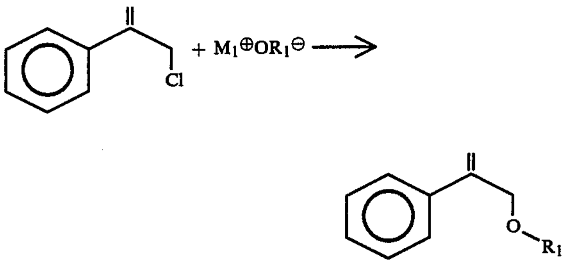

$R_1$ may be acetyl, propenyl, butyryl or benzoyl. The phase transfer agent is a quaternary ammonium salt such as ALIQUAT ® 336 marketed by the Henkel Corporation of Minneapolos, Minn. and more fully described in U.S. Pat. No. 4,010,207. This reaction is preferably carried out at reflux conditions in a solvent or in the absence of a solvent.

With respect to the reaction:

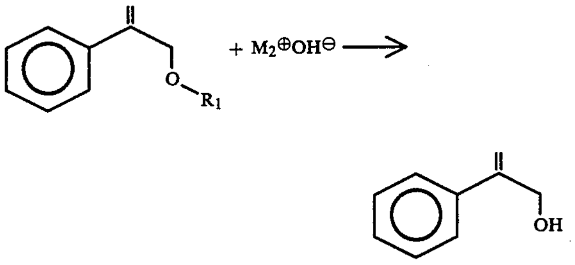

this reaction is carried out using 1.2 up to 2 equivalents of an alkali metal hydroxide such as sodium hydroxide or potassium hydroxide (10–30% in water) and may be carried out in the presence of a solvent or in the absence of a solvent, said solvent being, for example, a lower alkanol such as methyl alcohol or ethyl alcohol as stated, supra.

It will be appreciated from the present disclosure that the beta-alkylidene phenethyl alcohols of our invention can be used to alter, vary, fortify, modify, enhance or otherwise improve the aroma of a wide variety of materials particularly including perfume compositions, perfumed articles and perfumed polymers.

Thus, the beta-alkylidene phenethyl alcohols of our invention can be used to contribute lilac, rose, hyacinth, peony, green, cinnamon, honey and floral aromas with intense green, lilac, rose and hyacinth undertones to perfume compositions, perfumed articles and perfumed polymers.

As olfactory agents the beta-alkylidene phenethyl alcohols of our invention can be formulated into or used as components of a "perfume composition".

The "perfume composition" is used herein to mean a mixture of organic compounds, including, for example, alcohols other than the alcohols of this invention, aldehydes, ketones, nitriles, esters, and frequently hydrocarbons which are admixed so that the combined odors of the individual components produce a pleasant or desired fragrance. Such perfume compositions usually contain: (a) the main note of the "bouquet" or foundation-stone of the composition; (b) modifiers which round off and accompany the main note; (c) fixatives which include odorous substances which lend a particular note to the perfume throughout all stages of evaporation, and substances which retard evaporation; and (d) topnotes which are usually low-boiling, fresh-smelling materials.

In perfume compositions, the individual component will contribute its particular olfactory characteristics but the overall effect of the perfume composition will be the sum of the effect of each ingredient. Thus, the individual compounds of this invention, or mixtures thereof, can be used to alter the aroma characteristics of a perfume composition, for example, by highlighting or moderating the olfactory reaction contributed by another ingredient in the composition.

The amount of beta-alkylidene phenethyl alcohols of our invention which will be effective in perfume compositions depends on many factors, including the other ingredients, their amounts and the effects which are desired. It has been found that perfume compositions containing as little as 0.05% and as much as 50% of the beta-alkylidene phenethyl alcohols of our invention can be used to impart, augment or enhance lilac, rose, hyacinth, peony, green, cinnamon, honey and floral aromas with intense green, lilac, rose and hyacinth undertones in soaps, cosmetics, solid or liquid anionic, cationic, nonionic or zwitterionic detergents in other products. The amount employed can range up to 70% of the fragrance and can be as low as 1% of the original fragrance and will depend on considerations of cost, nature of the end product, the effect desired and the finished product and the particular fragrance sought.

The beta-alkylidene phenethyl alcohols or our invention can be used alone or in a perfume composition as as olfactory component in detergents, and soaps, space odorants and deodorants, perfumes, colognes, toilet waters, bath salts, hair preparations such as lacquers, brilliantines, pomades, and shampoos, cosmetic preparations such as creams, deodorants, hand lotions and sun screens, powders such as talcs, dusting powders, face powders, and the like.

When used as an olfactory component of a perfumed article, as little as 0.05% of one or more of the beta-alkylidene phenethyl alcohols of our invention will suffice to impart lilac, rose, hyacinth, peony, green, cinnamon, honey and floral aromas with intense green, lilac, rose and hyacinth undertones. Generally no more than 5.0% is required based on the perfumed article. Accordingly, the range in the perfumed article may vary from about 0.05% up to about 5.0% of the beta-alkylidene phenethyl alcohols of our invention.

In addition, the perfume composition can contain a vehicle or carrier for the beta-alkylidene phenethyl alcohols taken alone or together with other ingredients. The vehicle can be a liquid such as an alcohol such as ethanol, a glycol such as propylene glycol, or the like. The carrier can be an absorbent solid such as gum or a microporous polymer or components for encapsulating the composition such as by means of coacervation.

The following Examples I(A), I(B) and II are given to illustrate techniques for producing the beta-alkylidene phenethyl alcohols of our invention. The examples following Example II, that is, Examples III and onward are given to illustrate embodiments of our invention as it is presently preferred to practice it insofar as utilizing the beta-alkylidene phenethyl alchols of our invention for their organoleptic properties. It will be understood that these examples are illustrative and the invention is not to be considered restricted thereto except as indicated in the appended claims.

EXAMPLES I

Preparation of Beta-methylene phenethyl alcohol

EXAMPLE I(A)

STEP 1

Reaction:

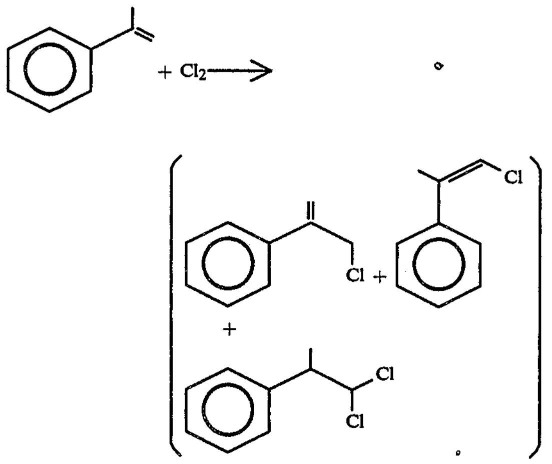

Into a 2 liter reaction vessel equipped with stirrer, thermometer, reflux condenser and chlorine feed line are placed 190 grams of sodium carbonate, 420 grams of alpha-methyl styrene and 400 ml of methylene dichloride. While maintaining the reaction mass at 25° C., chlorine gas is fed into the reaction mass over a period of one hour (with carbon dioxide evolution). At the end of the one hour chlorine feed time, the reaction mass is washed with water for use in Step 2.

FIG. 1 is the GLC profile for the reaction product of Step 1. The peak indicated by reference numeral 10 is the peak for $CHCl_3$. The peak indicated by reference numeral 11 is the peak for the compounds having the structures:

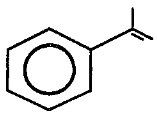
and
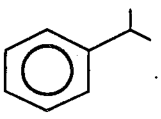
.

The peak indicated by reference numeral 12 is the peak for the compound having the structure:

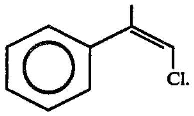

The peak indicated by reference numeral 13 is the peak for the compound having the structure:

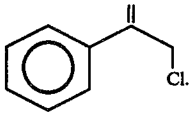

The peak indicated by reference numeral 14 is the peak for the compound having the structure:

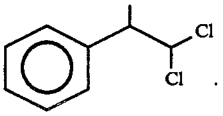

FIG. 2 is the NMR spectrum for the reaction product of Example I(A), a trap of peaks 12 and 13 of FIG. 1. The NMR spectrum is thus for the compounds having the structures:

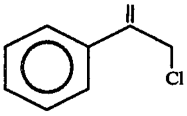
and
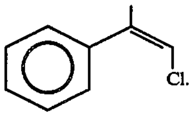

The weight ratio of compound having the structure:

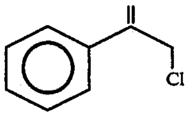

to the compound having the structure:

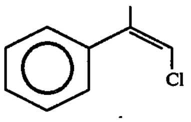

is approximately 3:2.

EXAMPLE I(A)

STEP 2

Reaction:

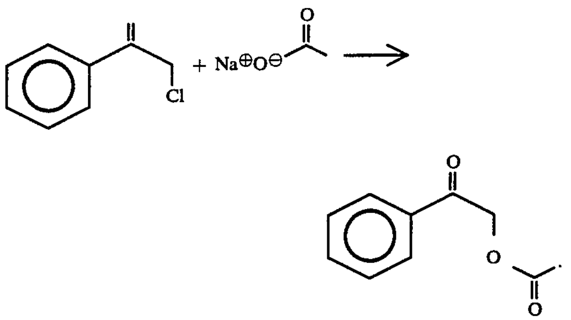

Into a 1 liter reaction vessel equipped with reflux condenser, thermometer and heating mantle is placed and organic phase of Step 1, supra containing the compounds having the structures:

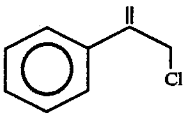
and
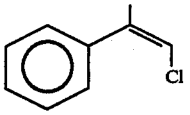

and in addition 291 grams of sodium acetate and 15 grams of ALIQUAT 336®. The reaction mass is heated to 80° C. and maintained at 80° C. for a period of one hour. At the end of the one hour period, the reaction mass is distilled on an 18" Goodloe column yielding the following fractions:

| Fraction No. | Vapor Temp. (°C.) | Liquid Temp. (°C.) | Vacuum mm/Hg. Pressure | % Acetate |
|---|---|---|---|---|
| 1 | 23/65 | 23/88 | 120/10 | — |
| 2 | 70 | 92 | 12.0 | — |
| 3 | 70 | 94 | 12.0 | — |
| 4 | 73 | 96 | 12.0 | — |
| 5 | 74 | 100 | 12.0 | 1 |
| 6 | 85 | 101 | 10.0 | 16 |
| 7 | 75 | 108 | 10.0 | — |
| 8 | 75 | 100 | 10.0 | 47 |
| 9 | 75 | 108 | 10.0 | 75 |
| 10 | 99 | 113 | 10.0 | 73 |
| 11 | 100 | 113 | 10.0 | 69 |
| 12 | 100 | 113 | 10.0 | 74 |
| 13 | 100 | 113 | 10.0 | 76 |
| 14 | 102 | 113 | 11.0 | — |
| 15 | 102 | 113 | 12.0 | — |
| 16 | 102 | 113 | 12.0 | — |
| 17 | 102 | 113 | 16.0 | — |
| 18 | 102 | 113 | 10.0 | — |
| 19 | 102 | 113 | 10.0 | 97 |
| 20 | 100 | 110 | 8.0 | — |
| 21 | 100 | 108 | 8.0 | — |
| 22 | 90 | 108 | 4.5 | 99 |
| 23 | 90 | 108 | 4.5 | 100 |
| 24 | 88 | 107 | 4.2 | 100 |
| 25 | 88 | 107 | 4.1 | 100 |
| 26 | 88 | 107 | 4.0 | 100 |
| 27 | 88 | 108 | 4.0 | 100 |
| 28 | 88 | 109 | 3.9 | 100 |
| 29 | 88 | 112 | 3.9 | 100 |
| 30 | 88 | 118 | 3.9 | 100 |
| 31 | 90 | 139 | 4.2 | 100 |
| 32 | 90 | 165 | 6.0 | — |
| 33 | 88 | 180 | 4.0 | — |

Fractions 22-31 are bulked for use in Example I(B).

FIG. 3 is the GLC profile for the reaction product of Step 2 of this Example I(A). The peak indicated by reference numeral 30 is the peak for $CHCl_3$. The peak indicated by reference 31 is the peak for the compounds having the structures:

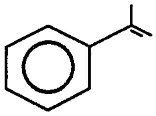
and
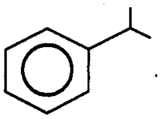
.

The peak indicated by reference numeral 32 is the peak for the compound having the structure:

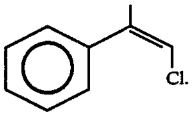
.

The peak indicated by reference numeral 33 is the peak for the compound having the structure:

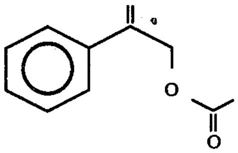

(Conditions: SE-30 column programmed at 180° C. isothermol).

The peak indicated by reference numeral 33 on FIG. 3 is trapped. FIG. 4 is the NMR spectrum for the peak indicated by reference numeral 33 on FIG. 3 and is for the compound having the structure:

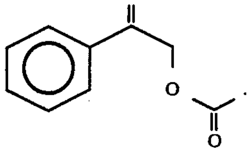
.

EXAMPLE I(B)

Reaction:

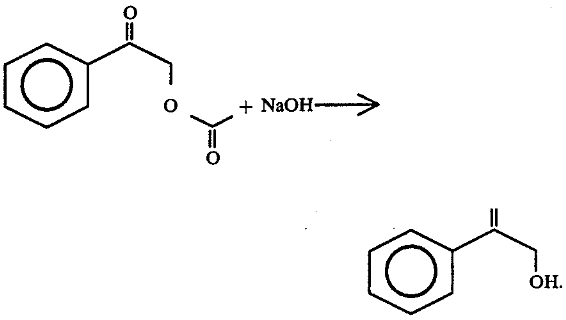

Into a 2 liter reaction vessel equipped with stirrer, thermometer, reflux condenser and heating mantle are placed 500 grams of the reaction product of Example I(A) containing the compound having the structure:

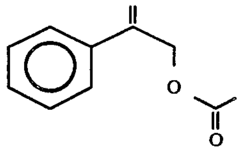

320 grams of an aqueous solution of 50% sodium hydroxide; 80 grams of water and 150 grams of methyl alcohol. The reaction mass is heated to reflux (temperature=92° C.) and maintained at reflux for a period of four hours. At the end of the four hour period, the reaction mass is cooled to room temperature and washed with water. The organic phase is then distilled on a Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 27/25 | 23/110 | 150/4 | 100% |
| 2 | 80 | 100 | 4.1 | 9:1 |
| 3 | 88 | 100 | 3.5 | 9:1 |
| 4 | 88 | 100 | 3.5 | 9:1 |
| 5 | 88 | 100 | 3.5 | 4:1 |
| 6 | 88 | 100 | 3.5 | 4:1 |
| 7 | 88 | 100 | 3.5 | 4:1 |
| 8 | 88 | 100 | 3.5 | 4:1 |
| 9 | 78 | 100 | 3.5 | 3:1 |
| 10 | 78 | 100 | 3.5 | 3:1 |
| 11 | 88 | 100 | 3.5 | 3:1 |
| 12 | 80 | 118 | 3.5 | 3:1 |
| 13 | 80 | 168 | 3.5 | — |

The resulting product has a lilac, rose, hyacinth, peony, green, cinnamon and honey aroma with intense green, lilac, rose and hyacinth undertones. Of particular interest is the "natural" floral nuance of this material.

FIG. 5 is the GLC profile of the crude reaction mixture. The peak indicated by reference numeral 50 is the peak for the compound having the structure:

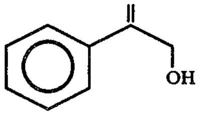

(Conditions: SE-30 column programmed at 180° C. isothermol).

FIG. 6 is the NMR spectrum for the compound having the structure:

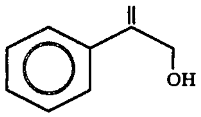

EXAMPLE II

Preparation of Beta-ethylidene phenethyl alcohol

Reaction:

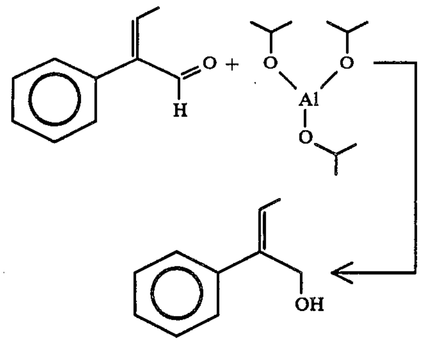

Into a 3 liter reaction vessel equipped with stirrer, reflux condenser, thermometer and heating mantle are placed 2000 grams of isopropyl alcohol and 75 grams of aluminum triisopropylate. The resulting mixture is heated to reflux and while refluxing, over a period of 1.5 hours, 500 grams of the aldehyde having the structure:

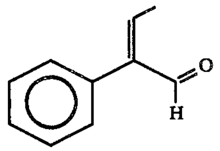

is added slowly to the reaction mass. At the end of the feed period of the aldehyde, solvent is commenced to be stripped at the ratio of 3:1 to a pot temperature of 130° C. The stripping takes place over a period of 5.5 hours. At the end of the 5.5 hour period, the reaction mass is cooled to 80° C. and 500 ml toluene and 150 grams of 50% aqueous sodium hydroxide and 150 grams of water is added to the reaction mass. The reaction mass is refluxed for a period of one hour and then cooled to room temperature.

The reaction mass is washed with 5% aqueous sodium hydroxide and the organic phase is distilled yielding the following fractions (on a Goodloe column):

| Fraction No. | Vapor Temp. (C.) | Liquid Temp. (C.) | Vacuum mm/Hg. Pressure | Reflux Ratio |
|---|---|---|---|---|
| 1 | 23/25 | 23/115 | 200/4 | 100% |
| 2 | 85 | 103 | 2.4 | 9:1 |
| 3 | 85 | 103 | 2.4 | 9:1 |
| 4 | 87 | 103 | 2.4 | 9:1 |
| 5 | 87 | 103 | 2.4 | 9:1 |
| 6 | 87 | 103 | 2.4 | 9:1 |
| 7 | 87 | 103 | 2.4 | 9:1 |
| 8 | 87 | 103 | 2.4 | 9:1 |
| 9 | 87 | 105 | 2.4 | 9:1 |
| 10 | 83 | 106 | 2.2 | 9:1 |
| 11 | 84 | 106 | 2.2 | 9:1 |
| 12 | 82 | 108 | 2.2 | 4:1 |
| 13 | 82 | 108 | 2.2 | 4:1 |
| 14 | 82 | 110 | 2.2 | 4:1 |
| 15 | 81 | 115 | 2.2 | 4:1 |
| 16 | 81 | 132 | 2.2 | 4:1 |
| 17 | 80 | 180 | 2.2 | 4:1 |

FIG. 7 is the GLC profile for the reaction product of this example containing the compound having the structure:

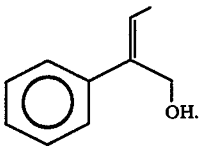

The peak indicated by reference numeral 70 is the peak for the compound having the structure:

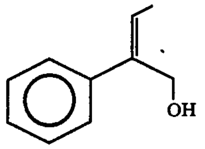

(Conditions: Carbowax column programmed at 180° C. isothermol).

FIG. 8 is the NMR spectrum for the compound having the structure:

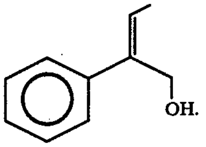

The compound having the structure:

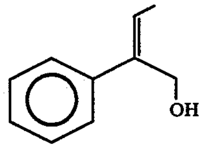

has an excellent aesthetically pleasing green, floral aroma with green and rose undertones.

EXAMPLE III

Perfume Formulation

The following floral/vetiver perfume formulation is prepared:

| Ingredients | Parts by Weight III(A) | III(B) |
|---|---|---|
| Vetivone | 25.0 | 25.0 |
| Compound having the structure: 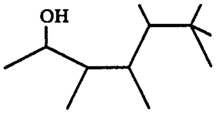 produced according to Example III of U.S. Letters Patent 4,391,999, bulked fractions 12-15. | 25.0 | 25.0 |
| Vetiverol | 5.0 | 5.0 |
| Musk Ketone | 8.0 | 8.0 |
| Styrax essence | 1.25 | 12.5 |

-continued

| Ingredients | Parts by Weight III(A) | III(B) |
|---|---|---|
| Geraniol | 32.4 | 32.4 |
| Phenylethyl alcohol | 12.8 | 12.8 |
| Compound having the structure: 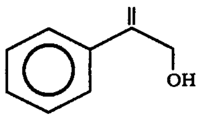 produced according to Example I(B). | 15.0 | — |
| Compound having the structure: 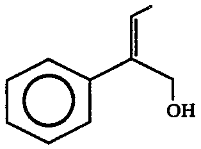 produced according to Example II. | — | 15.0 |

The perfume composition of Example III(A) has a floral and vetiver aroma with lilac, rose, hyacinth, peony, green, cinnamon and honey topnotes and green, lilac, rose and hyacinth undertones.

The perfume composition of Example III(B) has a vetiver and floral aroma with green and floral (rose) topnotes and green and rose undertones.

EXAMPLE IV

Perfumed Liquid Detergent

Concentrated liquid detergents with aromas as described in Table I below (which detergents are produced from the lysine salt of n-dodecyl benzene sulfonic acid as more specifically described in U.S. Pat. No. 3,948,818 issued on Apr. 6, 1976) are prepared containing one of the substances set forth in Table I below. They are prepared by adding and homogeneously mixing the appropriate quantity of substance as indicated in Table I below. The detergents all possess aroma profiles as set forth in Table I below, the intensity increasing with greater concentrations of the composition of matter as set forth in Table I below:

TABLE I

| Aroma Ingredient | Aroma Profile |
|---|---|
| The compound having the structure: 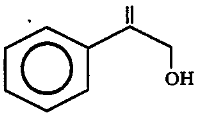 produced according to Example I(B). | A lilac, rose, hyacinth, peony, green, cinnamon and honey aroma with intense green, lilac, rose and hyacinth undertones. |

TABLE I-continued

| Aroma Ingredient | Aroma Profile |
|---|---|
| Compound having the structure: 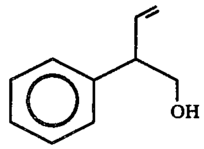 produced according to Example II. | A green and floral aroma with green and rose undertones. |
| Perfume composition of Example III(A). | Has a floral and vetiver aroma with lilac, rose, hyacinth, peony, green, cinnamon and honey topnotes and green, lilac, rose and hyacinth undertones. |
| Perfume composition of Example III(B). | Has a vetiver and floral aroma with green and floral (rose) topnotes and green and rose undertones. |

EXAMPLE V

Preparation of a Cologne and Handkerchief Perfume

Aroma imparting and augmenting ingredients as defined according to Table I of Example IV are incorporated into colognes at concentrations of 1.5%, 2.0%, 2.5%, 3.0%, 4.0% and 5.0% in 75%, 80%, 90% and 95% solutions of aqueous ethanol; and into handkerchief perfumes at concentrations of 15%, 20%, 25% and 30% (in 80%, 85% and 95% aqueous ethanol solutions). The use of the compositions of matter as set forth in Table I of Example IV affords distinct and definitive aroma profiles as set forth in Table I of Example IV to the handkerchief perfumes and to the colognes.

EXAMPLE VI

Preparation of a Soap Composition

One hundred grams of soap chips (IVORY ® manufactured by the Procter & Gamble Company of Cincinnati, Ohio, are melted and intimately admixed with one of the aroma materials as set forth in Table I of Example IV, supra, the amount of composition of matter of Table I of Example IV being one gram of each composition of matter. The conditions of mixing are: 180° C., 3 hours, 12 atmospheres pressure. At the end of the mixing cycle, while the soap is still under 12 atmospheres pressure, the mixture of soap and perfume of ingredient is cooled to room temperature. At this temperature, the resulting mixture is in a solid state. The resulting soap block is then cut up into soap cakes. Each of the soap cakes manifests an excellent aroma as set forth in Table I of Example IV. None of the soap samples show any discoloration even after two weeks in the oven at 90° F.

EXAMPLE VII

Preparation of a Detergent Composition

A total of 100 grams of a detergent powder (nonionic detergent powder containing a proteolytic enzyme prepared according to Example I of Canadian Pat. No. 985,190 issued on Mar. 9, 1976) is mixed with 0.15 grams of one of the compositions of matter as set forth in Table I of Example IV until a substantially homogeneous composition is obtained. Each of the compositions has excellent aroma profiles as set forth in Table I of Example IV.

EXAMPLE VIII

Perfumed Liquid Detergents

Concentrated liquid detergents with rich, pleasant aromas as set forth in Table I of Example IV are prepared containing 0.10%, 0.15% and 0.20% of each of the compositions of matter set forth in Table I of Example IV. They are prepared by adding and homogeneously admixing the appropriate quantity of composition of matter of Table I of Example IV in the liquid detergent. The liquid detergents are all produced using anionic detergents containing a 50:50 mixture of sodium lauroyl sarcosinate and potassium N-methyl lauroyl tauride. The detergents all possess pleasant aromas as defined in Table I of Example IV, the intensity increasing with greater concentrations of composition of matter of Table I of Example IV.

What is claimed is:

1. A process for augmenting or enhancing the aroma of a consumable material selected from the group consisting of perfume compositions, perfumed articles and perfumed polymers comprising the step of adding to said consumable material, an aroma augmenting or enhancing quantity of at least one compound defined according to the structure:

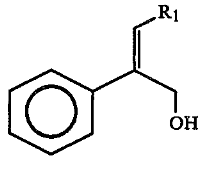

wherein $R_1$ is hydrogen or methyl.

2. The process of claim 1 wherein the consumable material is a perfume composition.

3. The process of claim 1 wherein the consumable material is a perfumed article and the perfumed article is a solid or liquid anionic, cationic, nonionic or zwitterionic detergent.

4. The process of claim 1 wherein the consumable material is a perfumed polymer.

5. The process of claim 1 wherein the consumable material is a perfumed article and the perfumed article is a fabric softener composition or drier-added fabric softener article.

6. The process of claim 1 wherein in the molecule:

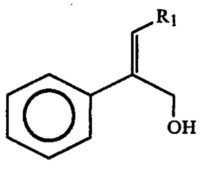

$R_1$ is hydrogen.

7. The process of claim 1 wherein in the molecule:

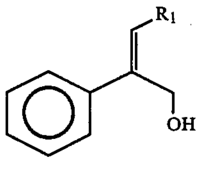

$R_1$ is methyl.

8. A process for preparing a compound having the structure:

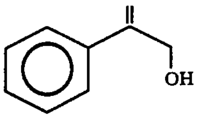

comprising the step of first reacting a halogen with alpha methyl styrene according to the reaction:

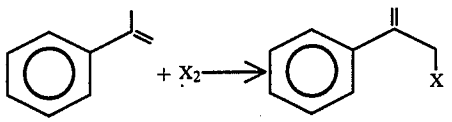

wherein X is chloro or bromo and then reacting the resulting alpha methylene phenethyl halide with an alkali metal salt of a carboxylic acid according to the reaction:

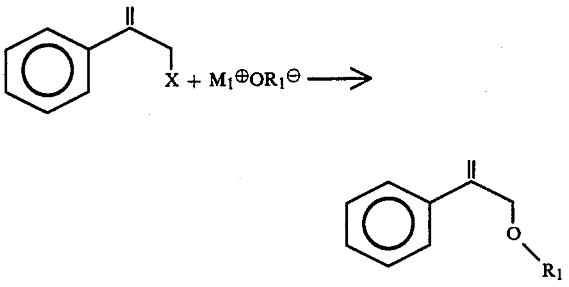

wherein $M_1$ is alkali metal and $R_1$ is $C_1$–$C_5$ acyl or benzoyl; and then hydrolyzing the resulting ester with an alkali metal hydroxide according to the reaction:

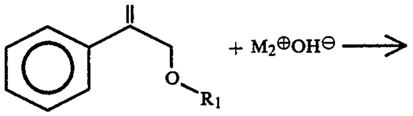

-continued

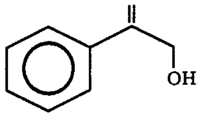

wherein $M_2$ is alkali metal, the same or different from $M_1$ and finally recovering the compound having the structure:

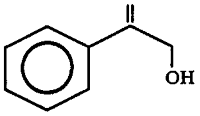

9. The process for preparing the compound having the structure:

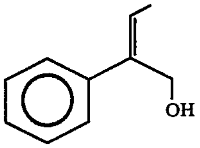

reacting the compound having the structure:

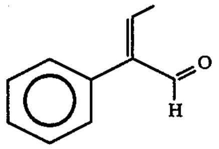

with aluminum triisopropylate and then recovering the compound having the structure:

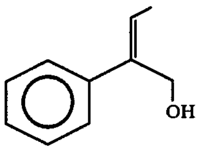

from the reaction mass.

* * * * *